United States Patent
Weser et al.

(10) Patent No.: US 10,328,001 B2
(45) Date of Patent: Jun. 25, 2019

(54) COMBINATIONS OF PRESERVATIVES FOR HAIR DYES

(71) Applicant: Henkel AG & Co. KGaA, Duesseldorf (DE)

(72) Inventors: Gabriele Weser, Neuss (DE); Rainer Simmering, Grevenbroich (DE); Mustafa Akram, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/379,174

(22) Filed: Dec. 14, 2016

(65) Prior Publication Data

US 2017/0172867 A1 Jun. 22, 2017

(30) Foreign Application Priority Data

Dec. 16, 2015 (DE) ........................ 10 2015 225 360

(51) Int. Cl.

| | |
|---|---|
| *A61Q 5/10* | (2006.01) |
| *A61K 8/23* | (2006.01) |
| *A45D 19/02* | (2006.01) |
| *A61K 8/34* | (2006.01) |
| *A61K 8/36* | (2006.01) |
| *A61K 8/368* | (2006.01) |
| *A61K 8/40* | (2006.01) |
| *A61K 8/41* | (2006.01) |
| *A61K 8/43* | (2006.01) |
| *A61K 8/44* | (2006.01) |
| *A61K 8/49* | (2006.01) |
| *A61K 8/58* | (2006.01) |
| *A61K 8/33* | (2006.01) |
| *A61K 8/42* | (2006.01) |
| *A61Q 19/06* | (2006.01) |
| *A45D 19/00* | (2006.01) |
| *A45D 7/00* | (2006.01) |

(52) U.S. Cl.
CPC ............... *A61K 8/23* (2013.01); *A45D 19/02* (2013.01); *A61K 8/33* (2013.01); *A61K 8/34* (2013.01); *A61K 8/345* (2013.01); *A61K 8/347* (2013.01); *A61K 8/36* (2013.01); *A61K 8/361* (2013.01); *A61K 8/368* (2013.01); *A61K 8/40* (2013.01); *A61K 8/41* (2013.01); *A61K 8/42* (2013.01); *A61K 8/43* (2013.01); *A61K 8/44* (2013.01); *A61K 8/49* (2013.01); *A61K 8/494* (2013.01); *A61K 8/498* (2013.01); *A61K 8/4926* (2013.01); *A61K 8/4946* (2013.01); *A61K 8/4953* (2013.01); *A61K 8/4966* (2013.01); *A61K 8/58* (2013.01); *A61Q 5/10* (2013.01); *A61Q 19/06* (2013.01); *A45D 2007/001* (2013.01); *A45D 2019/0083* (2013.01); *A61K 2800/43* (2013.01); *A61K 2800/87* (2013.01)

(58) Field of Classification Search
CPC ... A61Q 5/10; A61K 8/23; A61K 8/58; A61K 8/368; A61K 8/36; A61K 8/34; A61K 8/498; A61K 8/40; A61K 8/361; A61K 8/4953; A61K 8/347; A61K 8/4926; A61K 8/4946; A61K 8/49; A61K 8/43; A61K 8/44; A61K 8/41; A61K 2800/87; A45D 19/02
See application file for complete search history.

(56) References Cited

U.S. PATENT DOCUMENTS

| | | | |
|---|---|---|---|
| 2002/0010970 A1* | 1/2002 | Cottard | A61K 8/342 8/405 |
| 2004/0170590 A1* | 9/2004 | Fahnestock | A61K 8/64 424/70.14 |
| 2005/0166337 A1* | 8/2005 | Adam | A61K 8/40 8/406 |
| 2007/0186357 A1* | 8/2007 | Chalmers | A61K 8/19 8/405 |

* cited by examiner

*Primary Examiner* — Eisa B Elhilo
(74) *Attorney, Agent, or Firm* — James J. Cummings

(57) ABSTRACT

A cosmetic product for changing the color of keratin fibers, in particular human hair, includes a coloring preparation (F) that is packaged in a reclosable container (C), wherein the coloring preparation (F) includes, in a cosmetic carrier, (a) at least one first preservative from the group of sodium sulfite, potassium sulfite, potassium hydrogen sulfite, sodium hydrogen sulfite, zinc pyrithione, benzoic acid, salicylic acid, sorbic acid, formic acid, propionic acid and the physiologically acceptable salts of the aforementioned acids, and (b) at least one second preservative from the group of 2-phenoxyethanol, benzyl alcohol, 1-phenoxypropan-2-ol, isopropanol and ethanol, and (c) at least one oxidation dye precursor and/or one substantive dye.

A method for changing the color of the hair at the roots of the hair involves the use of such a product.

16 Claims, No Drawings

COMBINATIONS OF PRESERVATIVES FOR HAIR DYES

FIELD OF THE INVENTION

The present invention generally relates to cosmetic products for changing the color of keratin fibers, including a coloring preparation which is packaged in a reclosable container and which includes preservatives and also a color-imparting compound.

The present invention also relates to a method for changing the color of the hair at the roots of the hair, in which such products are used.

BACKGROUND OF THE INVENTION

Due to their composition, cosmetic agents can serve as a nutrient for germs and microorganisms. These germs can on the one hand cause microbial contamination of the consumer, and on the other hand they can alter the ingredients of the cosmetics and thereby form substances which have undesired effects such as sensitization or skin irritation. To prevent these undesired consequences and to ensure a particular shelf life of the cosmetics, said cosmetics must be preserved. Since preservatives in turn have the potential to cause irritation, the use thereof in cosmetics is strictly regulated.

Cosmetic products for changing the color of hair usually include substantive dyes and/or oxidation dye precursors. When using substantive dyes, the dye which already exists in finished form is applied to the keratin fibers.

Oxidation dye precursors are included in oxidative coloring agents. These involve so-called developer components and coupler components which together form the actual dyes only under the effect of oxidizing agents (usually hydrogen peroxide). Oxidative coloring agents are characterized by long-lasting color results.

Oxidative coloring agents are usually applied in an alkaline medium and require the presence of hydrogen peroxide. Since hydrogen peroxide itself has biocidal and preserving properties, it is usually not necessary to add further preservatives besides the hydrogen peroxide to oxidative color change agents. Under certain conditions, however, it may still be necessary to preserve oxidative coloring agents.

Oxidative coloring stresses the hair and is therefore usually repeated only after a period of 6 to 8 weeks. Over this time, however, the hair grows and the non-colored hair at the roots becomes visible. This difference in color between colored and non-colored hair is often perceived as highly unattractive by the consumer. One possibility for hiding these color differences is to color the roots. Coloring of the roots is carried out specifically only at the roots, for example 2 to 3 weeks after the regular coloring carried out on the full head of hair. Since this coloring of the roots takes place as an additional intermediate coloring between the regular coloring procedures carried out on the full head of hair, it creates an additional stress on the hair and should therefore be as gentle as possible. Root coloring agents therefore either include only substantive dyes, or else hydrogen peroxide is used in very low concentrations. The reduction of the concentration of hydrogen peroxide or the complete omission of the latter may make it necessary to use additional preservatives.

In addition, root coloring products are often presented in such a way that the quantity thereof is sufficient for treating the roots multiple times. The bottle or tube containing the color cream is repeatedly opened and closed by the user in order to withdraw the portion required for the individual root treatment, and therefore there is a risk of contamination of the product by germs or microorganisms. For this reason, too, a preserving of these coloring agents is necessary.

It is therefore desirable to discover effective preservative mixtures with good suitability for hair coloring agents. The intention for the preservatives is for such to be suitable for hair coloring agents for coloring the roots of the hair which are repeatedly opened and emptied in portions. The aim for the preservatives should be to prevent any colonization of the coloring agent or of the skin and scalp with undesired germs, while having no adverse effect or no significant adverse effect on the natural skin flora.

It is also desirable when using the preservatives in the coloring agent for the keratin fibers to be colored in bright intensive colors. In particular, it is desirable for no color shifts to occur as a result of using the preservatives, and for reactions between dyes and preservatives to be avoided, along with the formation of undesired by-products. In addition, it is desirable for the color-fastness properties not to be adversely affected by the use of the preservatives.

Furthermore, other desirable features and characteristics of the present invention will become apparent from the subsequent detailed description of the invention and the appended claims, taken in conjunction with this background of the invention.

BRIEF SUMMARY OF THE INVENTION

A cosmetic product for changing the color of keratin fibers, in particular human hair, includes a coloring preparation (F) which is packaged in a reclosable container (C), wherein the coloring preparation (F) includes, in a cosmetic carrier, at least one first preservative from the group consisting of sodium sulfite, potassium sulfite, potassium hydrogen sulfite, sodium hydrogen sulfite, zinc pyrithione, benzoic acid, salicylic acid, sorbic acid, formic acid, propionic acid and the physiologically acceptable salts of the aforementioned acids; at least one second preservative from the group consisting of 2-phenoxyethanol, benzyl alcohol, 1-phenoxypropan-2-ol, isopropanol and ethanol; and at least one oxidation dye precursor and/or one substantive dye.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that root coloring products can be optimally preserved and repeatedly applied if they comprise a coloring preparation (F) that includes at least one color-imparting substance (c), which coloring preparation is packaged in a reclosable container (C) and includes preservatives from at least two different groups (a) and (b).

A first subject matter of the present invention is a cosmetic product for changing the color of keratin fibers, in particular human hair, comprising
 a coloring preparation (F) which is packaged in a reclosable container (C), wherein the coloring preparation (F) includes, in a cosmetic carrier,
  (a) at least one first preservative from the group consisting of sodium sulfite, potassium sulfite, potassium hydrogen sulfite, sodium hydrogen sulfite, zinc pyrithione, benzoic acid, salicylic acid, sorbic acid, formic acid, propionic acid and the physiologically acceptable salts of the aforementioned acids, and
(b) at least one second preservative from the group consisting of 2-phenoxyethanol, benzyl alcohol, 1-phenoxypropan-2-ol, isopropanol and ethanol, and
(c) at least one oxidation dye precursor and/or one substantive dye.

Keratin fibers are to be understood to mean wool, fur, feathers and in particular human hair.

In the present invention, the terms keratinous fibers and keratin fibers are used synonymously. However, the coloring agents according to the invention may in principle also be used for coloring other natural fibers, such as for example cotton, jute, sisal, linen or silk, modified natural fibers, such as for example regenerated cellulose, nitrocellulose, alkyl cellulose, hydroxyalkyl cellulose or acetyl cellulose. With very particular preference, the agents according to the invention are agents for coloring hair.

The coloring preparation (F) includes the ingredients (a), (b) and (c) in a cosmetic carrier, preferably in a suitable aqueous or water-containing carrier. For the purpose of coloring hair, in particular for coloring roots, such carriers are for example creams, emulsions, gels or also surfactant-containing foaming solutions, such as for example shampoos, foam aerosols, foam formulations or other preparations which are suitable for use on the hair.

The term "color change agents" used according to the invention will be understood to mean coloring agents which change the hair color of the user. In particular, these are agents which are suitable for coloring roots. According to the invention, root coloring agents are gentle agents having a low hydrogen peroxide content and a pH in the neutral, weakly acidic or weakly alkaline range. Preferably, the root coloring agents may also be free of hydrogen peroxide (and other chemical oxidizing agents). According to the invention, root coloring agents are suitable for use at intervals of 1 to 2 weeks without causing excess damage to the hair.

The product according to the invention for coloring the roots of keratin fibers comprises at least one reclosable container (C), in which the coloring preparation (F) is packaged. This container (C) may be a bottle or tube or some other vessel. The size of the container (C) is selected in such a way that the container can hold a quantity of coloring preparation (F) sufficient for multiple root treatments. Preferably, the container (C) has a capacity of 10 to 500 ml. The feature of container (C) which is essential to the invention is the ability thereof to be reclosed, so that the coloring preparation (F) remaining after the first root treatment can continue to be stored in the container (C) and then can be used again at the time of the next root treatment.

The oxidation dye precursors optionally included in the coloring preparation (F) are sensitive to oxygen and therefore oxygen must as far as possible be prevented from entering the reclosed container (C). According to the invention, therefore, the reclosable container (C) has a cap which reduces or preferably prevents the ingress of oxygen. For repeat applications, a tube or bottle closed by a screw cap has proven to be suitable in particular. This screw cap may include a seal.

In one particularly preferred embodiment, the cosmetic product for changing the color of keratin fibers is therefore characterized in that the reclosable container (C) is a tube or bottle which is closed by a screw cap and which enables withdrawal of the coloring preparation (F) in portions.

The tube or bottle may be made for example of a polymeric plastic material or of metal (for example aluminum) and preferably has at one end a screw thread made of the tube material. The screw thread can be closed by a cap, preferably made of plastic or aluminum. A seal is preferably located in the cap.

The product according to the invention is particularly suitable for coloring the non-colored roots of the hair that has grown. The non-colored roots of the hair usually become visible approximately 1 to 3 weeks after the last coloring procedure and are formed by a narrow strip of non-colored hair having a width of from a few millimeters to at most 2 to 3 cm. In order to be able to apply the coloring agent preparation (F) to these non-colored roots in a targeted manner, the product preferably additionally comprises an applicator. This applicator may be shaped in various ways. Preferably, the dimensions of the applicator are selected in such a way that the applicator enables the coloring preparation (F) to be applied exclusively to the root region of the hair. By way of example, a comb having a width of at most 1 cm may be selected as the applicator. It is likewise possible to choose as the applicator a small sponge having a width adapted to the non-colored roots of the hair.

In one particularly preferred embodiment, the cosmetic product for changing the color of keratin fibers is therefore characterized in that it comprises an applicator for applying the coloring preparation (F) to the roots of the hair.

Preferably, an applicator device can be used for example to apply the coloring preparation (F), which applicator device has an application head and can be connected to the container (C) (for example by being screwed or plugged onto the latter). The application head may have a porous application body for applying the coloring preparation (F) by painting over the fibers.

For example, the applicator may be screwed onto the screw cap of the tube (that is to say of the container (C)). By pressing the tube, the coloring preparation (F) enters the porous application body in the applicator head of the applicator, is distributed there (for example through comb teeth or through a small sponge) and is applied to the keratin fibers of the roots by being painted onto the latter. At the end of the root coloring procedure, either the applicator can be unscrewed from the tube again and the tube can then be closed, or else the applicator remains on the tube and is closed with a tight fit and in an air-tight manner by a separate cap. This application form is particularly advantageous when the coloring preparation includes substantive dyes (c).

In one particularly preferred embodiment, the cosmetic product for changing the color is therefore characterized in that it comprises an applicator for applying the coloring preparation (F) to the roots of the hair, wherein the applicator has an application head with a porous application body.

The product according to the invention may additionally also comprise further containers. Particularly when the preparation (F) includes at least one oxidation dye precursor (c), it may be necessary to mix the coloring preparation (F) with an oxidizing agent preparation prior to the application to the roots. However, it is preferred when coloring the roots to use as few ingredients as possible which additionally damage the hair fibers.

In one very particularly preferred embodiment, therefore, the oxidation of the oxidation dye precursors takes place by means of oxygen in the air, that is to say that in this case the product comprises no further container containing hydrogen peroxide.

Another particularly preferred embodiment is a cosmetic product for changing the color of keratin fibers, in particular human hair, comprising a coloring preparation (F) which is packaged in a reclosable container (C), wherein the coloring preparation (F) includes, in a cosmetic carrier,
  (a) at least one first preservative from the group consisting of sodium sulfite, potassium sulfite, potassium hydrogen sulfite, sodium hydrogen sulfite, zinc pyrithione, benzoic acid, salicylic acid, sorbic acid, formic acid, propionic acid and the physiologically acceptable salts of the aforementioned acids, and
  (b) at least one second preservative from the group consisting of 2-phenoxyethanol, benzyl alcohol, 1-phenoxypropan-2-ol, isopropanol and ethanol, and
  (c) at least one oxidation dye precursor and/or one substantive dye,
wherein the product comprises no further container which includes hydrogen peroxide.

Furthermore, the product according to the invention may also comprise further containers which contain for example a shampoo, a conditioner or another pretreatment and/or aftertreatment agent.

Since the coloring preparation (F) is withdrawn in portions from the container (C) for repeated coloring of the roots, it includes for preserving purposes at least one preservative from group (a) and at least one preservative from group (b).

As a first constituent (a) which is essential to the invention, the coloring preparation includes at least one first preservative from the group consisting of sodium sulfite, potassium sulfite, potassium hydrogen sulfite, sodium hydrogen sulfite, zinc pyrithione, benzoic acid, salicylic acid, sorbic acid, formic acid, propionic acid and the physiologically acceptable salts of the aforementioned acids.

Sodium sulfite has the molecular formula $Na_2SO_3$.

Potassium sulfite has the molecular formula $K_2SO_3$.

Sodium hydrogen sulfite has the molecular formula $NaHSO_3$.

Potassium hydrogen sulfite has the molecular formula $KHSO_3$.

Zinc pyrithione is alternatively also known as zinc-bis[2-pyridinethiolate]-N,N'-dioxide or as 2-pyridinethiol 1-oxide, zinc salt and has the CAS number 13463-41-7.

Benzoic acid is alternatively also known as phenylformic acid or as phenylmethanoic acid and has the CAS number 65-85-0. The salts of benzoic acid, in particular the sodium salt and the potassium salt, are also encompassed by the invention.

Salicylic acid is alternatively also known as 4-hydroxybenzoic acid, p-salicylic acid or p-hydroxybenzoic acid and has the CAS number 99-96-7. The salts of salicylic acid, in particular the sodium salt and the potassium salt, are also encompassed by the invention.

Sorbic acid has the alternative names 2,4-hexadienoic acid ((2E,4E)-hexa-2,4-dienoic acid) and has the CAS number 110-44-1. The salts of sorbic acid, in particular the sodium salt and the potassium salt, are also encompassed by the invention.

Formic acid is alternatively also known as methanoic acid or formylic acid and has the CAS number 64-18-6. The salts of formic acid, in particular the sodium salt (sodium formate) and the calcium salt (calcium formate), are also encompassed by the invention.

Propionic acid is alternatively also known as propanoic acid and has the CAS number 79-09-4. The salts of propionic acid, in particular the sodium salt and the potassium salt, are also encompassed by the invention.

The coloring preparation (F) according to the invention further includes as a second constituent (b) which is essential to the invention at least one second preservative from the group consisting of 2-phenoxyethanol, benzyl alcohol, 1-phenoxypropan-2-ol, isopropanol and ethanol.

2-Phenoxyethanol is alternatively also known as 2-phenoxy-1-ethanol or ethylene glycol monophenyl ether and has the CAS number 122-99-6.

Benzyl alcohol is alternatively also known as phenylmethanol and has the CAS number 100-51-6.

1-Phenoxypropan-2-ol is alternatively also known as phenoxyisopropanol or 1-phenoxy-2-propanol and has the CAS number 770-35-4.

Isopropanol is alternatively also known as 2-propanol and has the CAS number 67-63-0.

Ethanol has the CAS number 64-17-5.

Both the preservative(s) (a) and the preservative(s) (b) should be used in sufficiently high quantities for an optimal preserving effect.

In a further embodiment according to the invention, the cosmetic product for changing the color of keratin fibers is therefore characterized in that it comprises a coloring preparation (F) which includes the preservatives (a) and (b) in a total amount that has a preserving effect.

In the context of the present invention, the "total amount that has a preserving effect" will be understood to mean that the total amount of all the preservatives from groups (a) and (b) which are included in the coloring preparation (F) is high enough that the coloring preparation (F) successfully passes the preservative challenge test.

Therefore, in the context of the present invention, a preservative effect will be understood to mean that the color cream (F) passes the preservative challenge test according to Ph. Eur. (European Pharmacopoeia), 6th edition, 5.3.1. The preservative challenge test is carried out as follows.

30 g of the coloring preparation (F) according to the invention that is to be tested were inoculated in each case with $10^5$ colony-forming units (CFUs) per 1 g composition of the following test microorganisms: *Pseudomonas aeruginosa* (bacterium), *Staphylococcus aureus* (bacterium), *Candida albicans* (fungus), *Aspergillus brasiliensis* (fungus). Following the addition of the respective microorganism, the sample was homogenized by stirring using a glass rod and then was stored in the dark at 20 to 25° C. After storage of the inoculated compositions for 7, 14, 21 or 28 days, in each case 1 g of the respective sample was removed and the CFUs included therein were determined. The aim of the preservation is to reduce the CFUs to a value below the detection limit (for each type of added microorganism). The preservative test is deemed to have been passed if the CFU is below the detection limit after 28 days at the latest.

If the preservatives according to the invention from groups (a) and (b) are used in particular amount ranges relative to one another, they may have a synergistic effect. In particular, if particular amount ratios are selected for the preservative(s) of group (a) and the preservative(s) of group (b), it is in this way possible to achieve a preserving effect that is greater than when one of the preservatives is used in the same amount. In this connection, it has proven to be very particularly advantageous if the preservatives from groups (a) and (b) are used in an amount ratio (a)/(b) of 10.0 to 0.1, preferably 5.0 to 0.2, more preferably 5.0 to 1.0 and very particularly preferably 2.5 to 0.4 in the coloring preparation (F).

In a further very particularly preferred embodiment, the cosmetic product for changing the color of keratin fibers is therefore characterized in that the weight ratio of all the preservatives (a) included in the coloring preparation (F) to all the preservatives (b) included in the coloring preparation (F), that is to say the weight ratio (a)/(b), is 10.0 to 0.1, preferably 5.0 to 0.2, more preferably 5.0 to 1.0 and very particularly preferably 2.5 to 0.4.

It has also proven to be very particularly advantageous if the coloring preparation (F) includes at least two preservatives (a) from the group consisting of sodium sulfite, potassium sulfite, potassium hydrogen sulfite, sodium hydrogen sulfite, zinc pyrithione, benzoic acid, salicylic acid, sorbic acid, formic acid, propionic acid and the physiologically acceptable salts of the aforementioned acids.

In a further very particularly preferred embodiment, the cosmetic product for changing the color of keratin fibers is therefore characterized in that the coloring preparation (F) includes at least two preservatives (a) from the group consisting of sodium sulfite, potassium sulfite, potassium hydrogen sulfite, sodium hydrogen sulfite, zinc pyrithione, benzoic acid, salicylic acid, sorbic acid, formic acid, propionic acid and the physiologically acceptable salts of the aforementioned acids.

Particular preference is therefore given to a cosmetic product for changing the color of keratin fibers, in particular human hair, comprising
  a coloring preparation (F) which is packaged in a reclosable container (C), wherein the coloring preparation (F) includes, in a cosmetic carrier,
(a) sodium sulfite and potassium sulfite,
(b) 2-phenoxyethanol,
(c) at least one oxidation dye precursor and/or one substantive dye.

Particular preference is also given to a cosmetic product for changing the color of keratin fibers, in particular human hair, comprising
  a coloring preparation (F) which is packaged in a reclosable container (C), wherein the coloring preparation (F) includes, in a cosmetic carrier,
(a) sodium sulfite and zinc pyrithione,
(b) 2-phenoxyethanol,
(c) at least one oxidation dye precursor and/or one substantive dye.

Particular preference is also given to a cosmetic product for changing the color of keratin fibers, in particular human hair, comprising
  a coloring preparation (F) which is packaged in a reclosable container (C), wherein the coloring preparation (F) includes, in a cosmetic carrier,
(a) sodium sulfite and benzoic acid,
(b) 2-phenoxyethanol,
(c) at least one oxidation dye precursor and/or one substantive dye.

Particular preference is also given to a cosmetic product for changing the color of keratin fibers, in particular human hair, comprising
  a coloring preparation (F) which is packaged in a reclosable container (C), wherein the coloring preparation (F) includes, in a cosmetic carrier,
(a) sodium sulfite and salicylic acid,
(b) 2-phenoxyethanol,
(c) at least one oxidation dye precursor and/or one substantive dye.

Particular preference is also given to a cosmetic product for changing the color of keratin fibers, in particular human hair, comprising
  a coloring preparation (F) which is packaged in a reclosable container (C), wherein the coloring preparation (F) includes, in a cosmetic carrier,
(a) sodium sulfite and sorbic acid,
(b) 2-phenoxyethanol,
(c) at least one oxidation dye precursor and/or one substantive dye.

Particular preference is also given to a cosmetic product for changing the color of keratin fibers, in particular human hair, comprising
  a coloring preparation (F) which is packaged in a reclosable container (C), wherein the coloring preparation (F) includes, in a cosmetic carrier,
(a) sodium sulfite and formic acid,
(b) 2-phenoxyethanol,
(c) at least one oxidation dye precursor and/or one substantive dye.

Particular preference is also given to a cosmetic product for changing the color of keratin fibers, in particular human hair, comprising
  a coloring preparation (F) which is packaged in a reclosable container (C), wherein the coloring preparation (F) includes, in a cosmetic carrier,
(a) sodium sulfite and propionic acid,
(b) 2-phenoxyethanol,
(c) at least one oxidation dye precursor and/or one substantive dye.

Particular preference is also given to a cosmetic product for changing the color of keratin fibers, in particular human hair, comprising
  a coloring preparation (F) which is packaged in a reclosable container (C), wherein the coloring preparation (F) includes, in a cosmetic carrier,
(a) sodium sulfite and benzoic acid,
(b) benzyl alcohol,
(c) at least one oxidation dye precursor and/or one substantive dye.

Particular preference is also given to a cosmetic product for changing the color of keratin fibers, in particular human hair, comprising
  a coloring preparation (F) which is packaged in a reclosable container (C), wherein the coloring preparation (F) includes, in a cosmetic carrier,
(a) sodium sulfite and salicylic acid,
(b) benzyl alcohol,
(c) at least one oxidation dye precursor and/or one substantive dye.

Particular preference is also given to a cosmetic product for changing the color of keratin fibers, in particular human hair, comprising
  a coloring preparation (F) which is packaged in a reclosable container (C), wherein the coloring preparation (F) includes, in a cosmetic carrier,
(a) sodium sulfite and sorbic acid,
(b) benzyl alcohol,
(c) at least one oxidation dye precursor and/or one substantive dye.

Particular preference is also given to a cosmetic product for changing the color of keratin fibers, in particular human hair, comprising
  a coloring preparation (F) which is packaged in a reclosable container (C), wherein the coloring preparation (F) includes, in a cosmetic carrier,
(a) sodium sulfite and formic acid,
(b) benzyl alcohol,
(c) at least one oxidation dye precursor and/or one substantive dye.

Particular preference is also given to a cosmetic product for changing the color of keratin fibers, in particular human hair, comprising a coloring preparation (F) which is packaged in a reclosable container (C), wherein the coloring preparation (F) includes, in a cosmetic carrier,
(a) sodium sulfite and propionic acid,
(b) benzyl alcohol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and potassium sulfite,
(b) 1-phenoxypropan-2-ol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and zinc pyrithione,
(b) 1-phenoxypropan-2-ol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and benzoic acid,
(b) 1-phenoxypropan-2-ol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and salicylic acid,
(b) 1-phenoxypropan-2-ol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and sorbic acid,
(b) 1-phenoxypropan-2-ol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and formic acid,
(b) 1-phenoxypropan-2-ol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and propionic acid,
(b) 1-phenoxypropan-2-ol,
(c) at least one oxidation dye precursor and/or one substantive dye.

LParticular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and potassium sulfite,
(b) isopropanol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and zinc pyrithione,
(b) isopropanol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and benzoic acid,
(b) isopropanol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and salicylic acid,
(b) isopropanol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and sorbic acid,
(b) isopropanol,
(c) at least one oxidation dye precursor and/or one substantive dye.

Particular preference is also given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite and formic acid, (b) isopropanol,
(c) at least one oxidation dye precursor and/or one substantive dye.

Particular preference is also given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sodium sulfite and propionic acid,
(b) isopropanol,
(c) at least one oxidation dye precursor and/or one substantive dye.

Particular preference is also given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sodium sulfite and potassium sulfite,
(b) ethanol,
(c) at least one oxidation dye precursor and/or one substantive dye.

Particular preference is also given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sodium sulfite and zinc pyrithione,
(b) ethanol,
(c) at least one oxidation dye precursor and/or one substantive dye.

Particular preference is also given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sodium sulfite and benzoic acid,
(b) ethanol,
(c) at least one oxidation dye precursor and/or one substantive dye.

Particular preference is also given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sodium sulfite and salicylic acid,
(b) ethanol,
(c) at least one oxidation dye precursor and/or one substantive dye.

Particular preference is also given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sodium sulfite and sorbic acid,
(b) ethanol,
(c) at least one oxidation dye precursor and/or one substantive dye.

Particular preference is also given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sodium sulfite and formic acid,
(b) ethanol,
(c) at least one oxidation dye precursor and/or one substantive dye.

Particular preference is also given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sodium sulfite and propionic acid,
(b) ethanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) potassium sulfite and zinc pyrithione,
(b) 2-phenoxyethanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) potassium sulfite and benzoic acid,
(b) 2-phenoxyethanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) potassium sulfite and salicylic acid,
(b) 2-phenoxyethanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) potassium sulfite and sorbic acid,
(b) 2-phenoxyethanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) potassium sulfite and formic acid,
(b) 2-phenoxyethanol,
(c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and propionic acid,
- (b) 2-phenoxyethanol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and benzoic acid,
- (b) benzyl alcohol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and salicylic acid,
- (b) benzyl alcohol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and sorbic acid,
- (b) benzyl alcohol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and formic acid,
- (b) benzyl alcohol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and propionic acid,
- (b) benzyl alcohol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and zinc pyrithione,
- (b) 1-phenoxypropan-2-ol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and benzoic acid,
- (b) 1-phenoxypropan-2-ol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and salicylic acid,
- (b) 1-phenoxypropan-2-ol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and sorbic acid,
- (b) 1-phenoxypropan-2-ol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and formic acid,
- (b) 1-phenoxypropan-2-ol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and propionic acid,
- (b) 1-phenoxypropan-2-ol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) potassium sulfite and zinc pyrithione,
- (b) isopropanol,
- (c) at least one oxidation dye precursor and/or one substantive dye.

Particular preference is therefore given to a cosmetic product for changing the color of keratin fibers, in particular human hair, comprising a coloring preparation (F) which is packaged in a reclosable container (C), wherein the coloring preparation (F) includes, in a cosmetic carrier,
(a) potassium sulfite and benzoic acid,
(b) isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite and salicylic acid,
(b) isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite and sorbic acid,
(b) isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite and formic acid,
(b) isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite and propionic acid,
(b) isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite and zinc pyrithione,
(b) ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite and benzoic acid,
(b) ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite and salicylic acid,
(b) ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite and sorbic acid,
(b) ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite and formic acid,
(b) ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite and propionic acid,
(b) ethanol,
(c) at least one oxidation dye precursor and/or one substantive dye.

It has also proven to be very particularly advantageous if the coloring preparation (F) includes at least two preservatives (b) from the group consisting of 2-phenoxyethanol, benzyl alcohol, 1-phenoxypropan-2-ol, isopropanol and ethanol.

In a further very particularly preferred embodiment, the cosmetic product for changing the color of keratin fibers is therefore characterized in that the coloring preparation (F) includes at least two preservatives (b) from the group consisting of 2-phenoxyethanol, benzyl alcohol, 1-phenoxypropan-2-ol, isopropanol and ethanol.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite,
(b) 2-phenoxyethanol and benzyl alcohol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier, (a) potassium sulfite,
(b) 2-phenoxyethanol and benzyl alcohol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium hydrogen sulfite,
(b) 2-phenoxyethanol and benzyl alcohol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium hydrogen sulfite,
(b) 2-phenoxyethanol and benzyl alcohol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) zinc pyrithione,
(b) 2-phenoxyethanol and benzyl alcohol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) benzoic acid,
(b) 2-phenoxyethanol and benzyl alcohol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) salicylic acid,
(b) 2-phenoxyethanol and benzyl alcohol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sorbic acid,
(b) 2-phenoxyethanol and benzyl alcohol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) formic acid,
(b) 2-phenoxyethanol and benzyl alcohol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) propionic acid,
(b) 2-phenoxyethanol and benzyl alcohol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite,
(b) 2-phenoxyethanol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite,
(b) 2-phenoxyethanol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium hydrogen sulfite,
(b) 2-phenoxyethanol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium hydrogen sulfite,
(b) 2-phenoxyethanol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) zinc pyrithione,
(b) 2-phenoxyethanol and 1-phenoxypropan-2-ol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) benzoic acid,
(b) 2-phenoxyethanol and 1-phenoxypropan-2-ol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) salicylic acid,
(b) 2-phenoxyethanol and 1-phenoxypropan-2-ol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sorbic acid,
(b) 2-phenoxyethanol and 1-phenoxypropan-2-ol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) formic acid,
(b) 2-phenoxyethanol and 1-phenoxypropan-2-ol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) propionic acid,
(b) 2-phenoxyethanol and 1-phenoxypropan-2-ol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sodium sulfite,
(b) 2-phenoxyethanol and isopropanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) potassium sulfite,
(b) 2-phenoxyethanol and isopropanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) potassium hydrogen sulfite,
(b) 2-phenoxyethanol and isopropanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sodium hydrogen sulfite,
(b) 2-phenoxyethanol and isopropanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) zinc pyrithione,
(b) 2-phenoxyethanol and isopropanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) benzoic acid,
(b) 2-phenoxyethanol and isopropanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) salicylic acid,
(b) 2-phenoxyethanol and isopropanol,
(c) at least one oxidation dye precursor and/or one substantive dye.

Particular preference is therefore given to a cosmetic product for changing the color of keratin fibers, in particular human hair, comprising
   a coloring preparation (F) which is packaged in a reclosable container (C), wherein the coloring preparation (F) includes, in a cosmetic carrier,
(a) sorbic acid,
(b) 2-phenoxyethanol and isopropanol,
(c) at least one oxidation dye precursor and/or one substantive dye.

Particular preference is therefore given to a cosmetic product for changing the color of keratin fibers, in particular human hair, comprising a coloring preparation (F) which is packaged in a reclosable container (C), wherein the coloring preparation (F) includes, in a cosmetic carrier,
(a) formic acid,
(b) 2-phenoxyethanol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) propionic acid,
(b) 2-phenoxyethanol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite,
(b) 2-phenoxyethanol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite,
(b) 2-phenoxyethanol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium hydrogen sulfite,
(b) 2-phenoxyethanol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium hydrogen sulfite,
(b) 2-phenoxyethanol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) zinc pyrithione,
(b) 2-phenoxyethanol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) benzoic acid,
(b) 2-phenoxyethanol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) salicylic acid,
(b) 2-phenoxyethanol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sorbic acid,
(b) 2-phenoxyethanol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) formic acid,
(b) 2-phenoxyethanol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) propionic acid,
(b) 2-phenoxyethanol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite,
(b) benzyl alcohol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite, (b) benzyl alcohol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium hydrogen sulfite,
(b) benzyl alcohol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium hydrogen sulfite,
(b) benzyl alcohol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) zinc pyrithione,
(b) benzyl alcohol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) benzoic acid,
(b) benzyl alcohol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) salicylic acid,
(b) benzyl alcohol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sorbic acid,
(b) benzyl alcohol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) formic acid,
(b) benzyl alcohol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) propionic acid,
(b) benzyl alcohol and 1-phenoxypropan-2-ol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite,
(b) benzyl alcohol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite,
(b) benzyl alcohol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium hydrogen sulfite,
(b) benzyl alcohol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium hydrogen sulfite,
(b) benzyl alcohol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) zinc pyrithione,
(b) benzyl alcohol and isopropanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) benzoic acid,
(b) benzyl alcohol and isopropanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) salicylic acid,
(b) benzyl alcohol and isopropanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) sorbic acid,
(b) benzyl alcohol and isopropanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) formic acid,
(b) benzyl alcohol and isopropanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) propionic acid,
(b) benzyl alcohol and isopropanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) sodium sulfite,
(b) benzyl alcohol and ethanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) potassium sulfite,
(b) benzyl alcohol and ethanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) potassium hydrogen sulfite,
(b) benzyl alcohol and ethanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) sodium hydrogen sulfite,
(b) benzyl alcohol and ethanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) zinc pyrithione,
(b) benzyl alcohol and ethanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) benzoic acid,
(b) benzyl alcohol and ethanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) salicylic acid,
(b) benzyl alcohol and ethanol,
(c) at least one oxidation dye precursor and/or one substantive dye.

Particular preference is therefore given to a cosmetic product for changing the color of keratin fibers, in particular human hair, comprising
 a coloring preparation (F) which is packaged in a reclosable container (C), wherein the coloring preparation (F) includes, in a cosmetic carrier,
(a) sorbic acid,
(b) benzyl alcohol and ethanol,
(c) at least one oxidation dye precursor and/or one substantive dye.

Particular preference is therefore given to a cosmetic product for changing the color of keratin fibers, in particular human hair, comprising a coloring preparation (F) which is packaged in a reclosable container (C), wherein the coloring preparation (F) includes, in a cosmetic carrier,
(a) formic acid,
(b) benzyl alcohol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) propionic acid,
(b) benzyl alcohol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite,
(b) 1-phenoxypropan-2-ol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite,
(b) 1-phenoxypropan-2-ol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium hydrogen sulfite,
(b) 1-phenoxypropan-2-ol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium hydrogen sulfite,
(b) 1-phenoxypropan-2-ol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) zinc pyrithione,
(b) 1-phenoxypropan-2-ol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) benzoic acid,
(b) 1-phenoxypropan-2-ol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) salicylic acid,
(b) 1-phenoxypropan-2-ol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sorbic acid,
(b) 1-phenoxypropan-2-ol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) formic acid,
(b) 1-phenoxypropan-2-ol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) propionic acid,
(b) 1-phenoxypropan-2-ol and isopropanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) sodium sulfite,
(b) 1-phenoxypropan-2-ol and ethanol,
(c) at least one oxidation dye precursor and/or one substantive dye.

Particular preference is therefore given to a cosmetic product for changing the color of keratin fibers, in particular human hair, comprising
a coloring preparation (F) which is packaged in a reclosable container (C), wherein the coloring preparation (F) includes, in a cosmetic carrier,
(a) potassium sulfite, (b) 1-phenoxypropan-2-ol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) potassium hydrogen sulfite,
(b) 1-phenoxypropan-2-ol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) sodium hydrogen sulfite,
(b) 1-phenoxypropan-2-ol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) zinc pyrithione,
(b) 1-phenoxypropan-2-ol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) benzoic acid,
(b) 1-phenoxypropan-2-ol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) salicylic acid,
(b) 1-phenoxypropan-2-ol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) sorbic acid,
(b) 1-phenoxypropan-2-ol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) formic acid,
(b) 1-phenoxypropan-2-ol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) propionic acid,
(b) 1-phenoxypropan-2-ol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) sodium sulfite,
(b) isopropanol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) potassium sulfite,
(b) isopropanol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) potassium hydrogen sulfite,
(b) isopropanol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) sodium hydrogen sulfite,
(b) isopropanol and ethanol,
(c) at least one oxidation dye precursor and/or one substantive dye.

Particular preference is therefore given to a cosmetic product for changing the color of keratin fibers, in particular human hair, comprising
    a coloring preparation (F) which is packaged in a reclosable container (C), wherein the coloring preparation (F) includes, in a cosmetic carrier,
(a) zinc pyrithione,
(b) isopropanol and ethanol,
(c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) benzoic acid,
- (b) isopropanol and ethanol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) salicylic acid,
- (b) isopropanol and ethanol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) sorbic acid,
- (b) isopropanol and ethanol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) formic acid,
- (b) isopropanol and ethanol,
- (c) at least one oxidation dye precursor and/or one substantive dye.

Particular preference is therefore given to a cosmetic product for changing the color of keratin fibers, in particular human hair, comprising
- a coloring preparation (F) which is packaged in a reclosable container (C), wherein the coloring preparation (F) includes, in a cosmetic carrier,
- (a) propionic acid,
- (b) isopropanol and ethanol,
- (c) at least one oxidation dye precursor and/or one substantive dye.

The coloring preparation (F) according to the invention particularly preferably includes—based on the total weight of the coloring preparation (F)—one or more preservatives (a) in a total amount of 0.05 to 4.5% by weight, preferably 0.1 to 1.8% by weight, more preferably 0.15 to 0.9% by weight and very particularly preferably 0.2 to 0.7% by weight. All amounts specified in % by weight refer to the total weight of all the preservatives of group (a) included in the coloring preparation (F) in relation to the total weight of the coloring preparation (F).

In a further very particularly preferred embodiment, the cosmetic product for changing the color of keratin fibers is therefore characterized in that the coloring preparation (F) includes—based on the total weight of the coloring preparation (F)—one or more preservatives (a) in a total amount of 0.05 to 4.5% by weight, preferably 0.1 to 1.8% by weight, more preferably 0.15 to 0.9% by weight and very particularly preferably 0.2 to 0.7% by weight.

Furthermore, the coloring preparation (F) according to the invention particularly preferably includes—based on the total weight of the coloring preparation (F)—one or more preservatives (b) in a total amount of 0.1 to 7.0% by weight, preferably 0.3 to 5.0% by weight, more preferably 0.5 to 4.5% by weight and particularly preferably 0.7 to 2.5% by weight. All amounts specified in % by weight refer to the total weight of all the preservatives of group (b) included in the coloring preparation (F) in relation to the total weight of the coloring preparation (F).

In a further very particularly preferred embodiment, the cosmetic product for changing the color of keratin fibers is therefore characterized in that the coloring preparation (F) includes—based on the total weight of the coloring preparation (F)—one or more preservatives (b) in a total amount of 0.1 to 7.0% by weight, preferably 0.3 to 5.0% by weight, more preferably 0.5 to 4.5% by weight and particularly preferably 0.7 to 2.5% by weight.

By adding a further preservative from a third group (d) to the coloring preparation (F), the preserving effect can be enhanced even further. The coloring preparation (F) therefore preferably additionally includes at least one further preservative (d) from the group formed of sorbic acid, 2-hydroxydiphenyl, 4-hydroxybenzoic acid, dehydroacetic acid, dibromohexamidine, 10-undecylenic acid, hexetidinum, triclocarban, triclosanum, 4-chloro-3,4-dimethylphenol, imidazolidinyl urea, hexamethylenetetramine, 1-(4-chlorophenoxy)-1-(imidazol-1-yl)-3,3-dimethyl-2-butanone, 1,3-bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3 (2H)-isothiazolone, 2-benzyl-4-chlorophenol, 2-chloroacetamide, chlorhexidine, 4,4-dimethyl-1,3-oxazolidine, 1-phenoxypropan-2-ol, hexamidinum, 5-ethyl-1-aza-3,7-dioxabicyclo-[3.3.0]-octane, chlorphenesin, sodium hydroxymethyl aminoacetate, benzyl hemiformal, 3-iodo-2-propynyl butylcarbamate, methylisothiazolinone and Ethyl Lauroyl Arginate.

In a further very particularly preferred embodiment, the cosmetic product for changing the color of keratin fibers is therefore characterized in that the coloring preparation (F) additionally includes at least one preservative from the group consisting of
(d) 2-hydroxydiphenyl, dehydroacetic acid, dibromohexamidine, 10-undecylenic acid, hexetidinum, triclocarban, triclosanum, 4-chloro-3,4-dimethylphenol, imidazolidinyl urea, hexamethylenetetramine, 1-(4-chlorophenoxy)-1-(imidazol-1-yl)-3,3-dimethyl-2-butanone, 1,3-bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl) phenol, 5-chloro-2-methyl-3(2H)-isothiazolone, 2-benzyl-4-chlorophenol, 2-chloroacetamide, chlorhexidine, 4,4-dimethyl-1,3-oxazolidine, 1-phenoxypropan-2-ol, hexamidinum, 5-ethyl-1-aza-3,7-dioxabicyclo-[3.3.0]-octane, chlorphenesin, sodium hydroxymethyl aminoacetate, benzyl hemiformal, 3-iodo-2-propynyl butylcarbamate, methylisothiazolinone and Ethyl Lauroyl Arginate.

2-Hydroxydiphenyl is alternatively also known as biphenyl-2-ol or 2-hydroxybiphenyl or orthophenylphenol. 2-Hydroxydiphenyl has the CAS number 90-43-7.

Dehydroacetic acid has the alternative names 3-acetyl-6-methyl-2,4(3H)-pyrandione, has the CAS number 520-45-6 and has the structure (K1). The tautomeric forms of dehydroacetic acid are also encompassed by the invention.

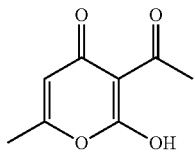
(K1)

Dibromohexamidine is alternatively also known as 1,6-bis(4-amidino-2-bromophenoxy)-n-hexane or as, 4'-(hexane-1,6-diyl)-bis-(3-bromobenzamidine) and has the CAS number 93856-82-7. Dibromohexamidine has the structure (K2).

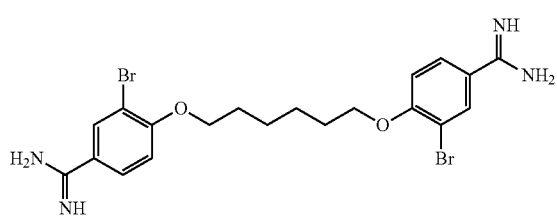
(K2)

10-Undecylenic acid has the alternative names undec-10-enoic acid or 10-undecenoic acid and has the CAS number 112-38-9. 10-Undecylenic acid has the structure of formula (K3). The salts of 10-undecylenic acid, in particular the sodium salt and the potassium salt, are also encompassed by the invention.

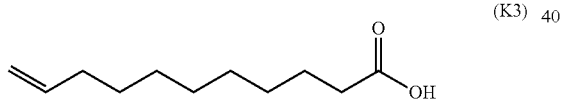
(K3)

Hexetidinum is alternatively also known as hexetidine or 1,3-bis(2-ethylhexyl)-5-methylhexahydropyrimidin-5-amine. Hexetidinum or hexetidine has the CAS number 141-94-6. Hexetidinum or hexetidine has the structure of formula (K4).

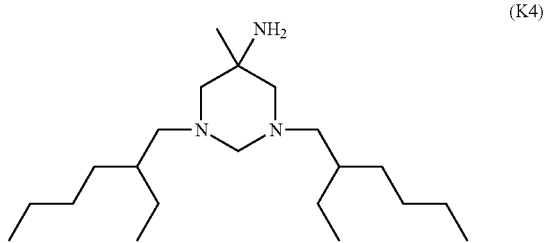 [SMILES: CCCCC(CC)CN1CN(CC(CC)CCCC)CC(C)(N)C1]
(K4)

Triclocarban also has the alternative names 3,4,4'-trichlorocarbanilide or 3-(4-chlorophenyl)-1-(3,4-dichlorophenyl)urea and has the CAS number 101-20-2. Triclocarban has the structure of formula (K5).

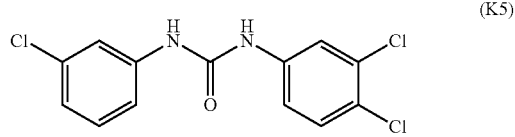 [SMILES: O=C(Nc1cccc(Cl)c1)Nc1ccc(Cl)c(Cl)c1]
(K5)

Triclosanum or triclosan is alternatively also known as 5-chloro-2-(2,4-dichlorophenoxy)phenol. Triclosanum or triclosan has the CAS number 3380-34-5. Triclosanum or triclosan has the structure of formula (K6).

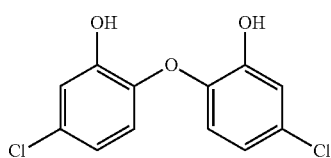
(K6)

4-Chloro-3,4-dimethylphenol is also known as chloroxylenol and has the CAS number 88-04-0.

Imidazolidinyl urea is alternatively also known as N,/N'-methylenebis[N'-(3-hydroxymethyl-2,5-dioxo-4-imidazolidinyl)urea]. Imidazolidinyl urea has the CAS number 39236-46-9 and has the structure of formula (K7).

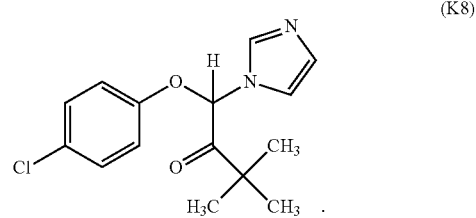 [SMILES: CC(C)(C)C(=O)C(Oc1ccc(Cl)cc1)n1ccnc1]
(K7)

Hexamethylenetetramine is also known as urotropine or 1,3,5,7-tetraazaadamantane. Hexamethylenetetramine has the CAS number 100-97-0.

1-(4-Chlorophenoxy)-1-(imidazol-1-yl)-3,3-dimethyl-2-butanone is alternatively also known as climbazole, has the CAS number 38083-17-9 and has a structure of formula (K8). The structure K8 comprises two enantiomeric forms. Both enantiomers and also the mixture of the two enantiomers are encompassed by the invention.

(K8)

1,3-Bis-(hydroxymethyl)-5,5-dimethyl-2,4-imidazolidinedione is also known as DMDM hydantoin, has the CAS number 6440-58-0 and has the structure of formula (K9).

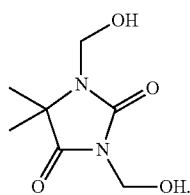

1-Hydroxy-4-methyl-6-(2,4,4-trimethylpentyl)-2-pyridone has the alternative names 1-hydroxy-4-methyl-6-(2,4,4-trimethylpentyl)pyridin-2(1H)-one, octopirox and piroctone olamine and has the CAS number 68890-66-4. With particular preference, this preservative is used in the form of its 1:1 adduct with 2-aminoethanol. 1-Hydroxy-4-methyl-6-(2,4,4-trimethylpentyl)-2-pyridone (in the form of its ethanolamine adduct) has the structure of formula (K10).

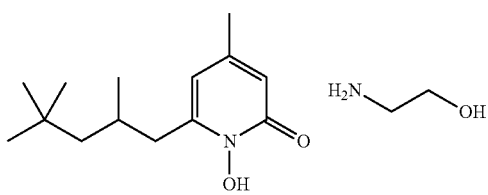

Bromochlorophene has the alternative name 2,2'-methylenebis-(6-bromo-4-chlorophenol) and has the CAS number 15435-29-7. Bromochlorophene has the structure of formula (K11).

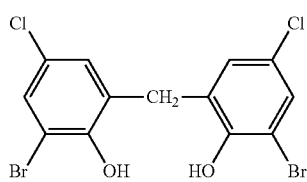

3-Methyl-4-(1-methylethyl)phenol has the alternative names o-cymen-5-ol, p-thymol, biosol and 1-hydroxy-3-methyl-4-isopropylbenzene and has the CAS number 3228-02-2.

5-Chloro-2-methyl-3(2H)-isothiazolone is alternatively also known as 5-chloro-2-methyl-4-isothiazolin-3-one or chloromethylisothiazolone, has the CAS number 26172-55-4 and has the structure of formula (K12).

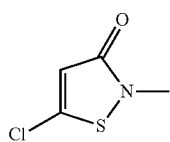

2-Benzyl-4-chlorophenol is alternatively also known as chlorophenum or chlorophene and has the CAS number 120-32-1.

2-Chloroacetamide has the alternative name chloroacetic acid amide and has the CAS number 79-07-2.

Chlorhexidine is alternatively also known as 1,1'-hexamethylenebis[5-(4-chlorophenyl)biguanide] and has the CAS number 55-56-1. Chlorhexidine has the structure of formula (K13).

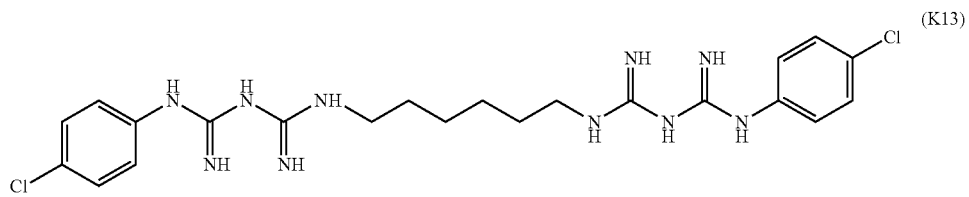 [SMILES: N=C(NCCCCCCNC(=N)NC(=N)Nc1ccc(Cl)cc1)NC(=N)Nc1ccc(Cl)cc1]

4,4-Dimethyl-1,3-oxazolidine has the CAS number 51200-87-4.

1-Phenoxypropan-2-ol is alternatively also known as phenyl-β-hydroxypropyl ether, 1-phenoxy-2-propanol, phenoxyisopropanol, propylene phenoxetol, 2-phenoxy-1-methylethanol or propylene glycol 1-phenyl ether and has the CAS number 770-35-4.

Hexamidinum is alternatively also known as hexamidine or 1,6-bis(4-amidinophenoxy)-n-hexane or 4,4'-[hexane-1,6-diylbis(oxy)]dibenzenecarboximidamide and has the CAS number 3811-75-4. Hexamidine has the structure of formula (K14).

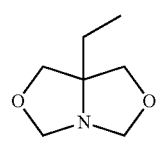

5-Ethyl-1-aza-3,7-dioxabicyclo-[3.3.0]-octane is alternatively also known as 5-ethyl-3,7-dioxa-1-azabicyclo[3.3.0]octane or dihydro-7a-ethyloxazolo[3,4-c]oxazole, has the CAS number 7747-35-5 and has the structure of formula (K15)

Chlorphenesin is alternatively also known as (3-(4-chlorophenoxy)-2-hydroxypropyl)carbamate and has the CAS number 886-74-8. Chlorphenesin has the structure of formula (K16).

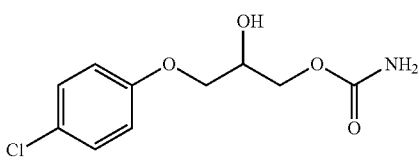
(K16)

Sodium hydroxymethyl aminoacetate is alternatively also known as sodium N-(hydroxymethyl)glycinate or sodium N-(hydroxymethyl)glycinate, has the CAS number 70161-44-3 and has the structure of formula (K17).

(K17)

Benzyl hemiformal is alternatively also known as (benzyloxy)methanol and has the CAS number 14548-60-8.

3-Iodo-2-propynyl butylcarbamate is alternatively also known as 3-iodopropargyl N-butylcarbamate or Biodocarb and has the CAS number 55406-53-6. 3-Iodo-2-propynyl butylcarbamate has the structure of formula (K18).

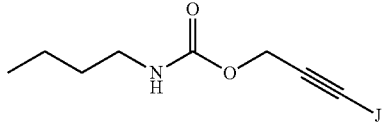
(K18)

Methylisothiazolinone is alternatively also known as 2-methyl-2H-isothiazol-3-one and has the CAS number 2682-20-4

Ethyl Lauroyl Arginate is alternatively also known as ethyl-Nα-dodecanoyl-L-arginate hydrochloride or monohydrochloride of L-arginine or Nα-lauroyl-ethyl ester and has the CAS number 60372-77-2. Ethyl Lauroyl Arginate has the structure of formula (K19) and can be used either as a free compound or in the form of its hydrochloride salt.

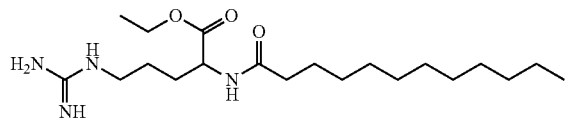
(K19)

The preservatives (d) according to the invention may also work together synergistically, so that using a combination of at least two preservatives of group (a) leads to a preserving effect that is greater than when the same amount of a single preservative is used.

In one very particularly preferred embodiment, the agent according to the invention for coloring keratin fibers therefore includes at least two preservatives (d) from the group consisting of 2-hydroxydiphenyl, dehydroacetic acid, dibromohexamidine, 10-undecylenic acid, hexetidinum, triclocarban, triclosanum, 4-chloro-3,4-dimethylphenol, imidazolidinyl urea, hexamethylenetetramine, 1-(4-chlorophenoxy)-1-(imidazol-1-yl)-3,3-dimethyl-2-butanone, 1,3-bis-(hydroxymethyl)-5, 5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3 (2H)-isothiazolone, 2-benzyl-4-chlorophenol, 2-chloroacetamide, chlorhexidine, 4,4-dimethyl-1,3-oxazolidine, 1-phenoxypropan-2-ol, hexamidinum, 5-ethyl-1-aza-3,7-dioxabicyclo-[3.3.0]-octane, chlorphenesin, sodium hydroxymethyl aminoacetate, benzyl hemiformal, 3-iodo-2-propynyl butylcarbamate, methylisothiazolinone and Ethyl Lauroyl Arginate.

In one particularly preferred embodiment, an agent according to the invention for coloring keratin fibers is characterized in that it contains (a) at least two preservatives from the group consisting of 2-hydroxydiphenyl, 4-hydroxybenzoic acid, dehydroacetic acid, dibromohexamidine, 10-undecylenic acid, hexetidinum, triclocarban, triclosanum, 4-chloro-3,4-dimethylphenol, imidazolidinyl urea, hexamethylenetetramine, 1-(4-chlorophenoxy)-1-(imidazol-1-yl)-3,3-dimethyl-2-butanone, 1,3-bis-(hydroxymethyl)-5, 5-dimethyl-2, 4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3 (2H)-isothiazolone, 2-benzyl-4-chlorophenol, 2-chloroacetamide, chlorhexidine, 4,4-dimethyl-1,3-oxazolidine, 1-phenoxypropan-2-ol, hexamidinum, 5-ethyl-1-aza-3,7-dioxabicyclo-[3.3.0]-octane, chlorphenesin, sodium hydroxymethyl aminoacetate, benzyl hemiformal, 3-iodo-2-propynyl butylcarbamate, methylisothiazolinone and Ethyl Lauroyl Arginate.

The above-described preservatives of groups (a) and (b) and also the further preferred combinations from groups (a), (b) and (d) can be used both for preserving coloring agents which include substantive dyes and for preserving coloring agents which include oxidation dye precursors.

In a further particularly preferred embodiment, a product according to the invention for changing the color of keratin fibers is characterized in that the coloring preparation (F) includes at least (c) one substantive dye.

Substantive dyes can be divided into anionic, cationic and nonionic substantive dyes. The substantive dyes are preferably selected from nitrophenylenediamines, nitroaminophenols, azo dyes, anthraquinones, triarylmethane dyes or indophenols and physiologically acceptable salts thereof. The additional substantive dyes are each preferably used in a proportion of 0.001 to 2% by weight, based on the total use preparation.

In a further particularly preferred embodiment, an agent according to the invention for coloring keratin fibers is characterized in that it includes at least one neutral substantive dye.

Suitable nonionic substantive dyes are in particular nonionic nitro and quinone dyes and neutral azo dyes. Preferred nonionic substantive dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4, 6-dinitro phenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureido-ethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

In a further particularly preferred embodiment, an agent according to the invention for coloring keratin fibers is characterized in that it includes as the substantive dye at least one cationic substantive dye.

Preferred cationic substantive dyes are cationic triphenylmethane dyes, such as for example Basic Blue 7, Basic Blue 26, Basic Violet 2 and Basic Violet 14, aromatic systems which are substituted with a quaternary nitrogen group, such as for example Basic Yellow 57, Basic Red 76, Basic Blue 99, Basic Brown 16 and Basic Brown 17, cationic anthraquinone dyes, such as HC Blue 16 (Bluequat B), as well as substantive dyes that include a heterocycle which has at least one quaternary nitrogen atom, in particular Basic Yellow 87, Basic Orange 31 and Basic Red 51. The cationic substantive dyes which are sold under the trademark Arianor are cationic substantive dyes which are likewise preferred according to the invention.

In a further particularly preferred embodiment, an agent according to the invention for coloring keratin fibers is characterized in that it includes as the substantive dye at least one anionic acid dye.

Preferred anionic substantive dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue and Tetrabromophenol Blue.

In particular, it is preferred if the compound(s) of formula (I) are used in combination with Basic Yellow 57, Basic Red 76, Basic Brown 16 and Basic Brown 17 such as HC Blue 16 (Bluequat B), Basic Yellow 87, Basic Orange 31, Basic Red 51, HC Red 1, HC Red 3, HC Red 7, HC Red 10, HC Red 11, HC Red 13, HC Red BN, HC Blue 2, HC Blue 11, HC Blue 12, 2-amino-4-nitrophenol, 1,4-bis-(2-hydroxyethyl)amino-2-nitrobenzene, 3-nitro-4-(2-hydroxyethyl)aminophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 4-[(3-hydroxypropyl)amino]-3-nitrophenol and/or 4-nitro-o-phenylendiamine.

The substantive dye(s) may be included in the agent according to the invention in a total amount of 0.0001 to 5.0% by weight, preferably 0.01 to 2.5% by weight, more preferably 0.05 to 1.0% by weight and very particularly preferably 0.1 to 0.9% by weight, based on the total weight of the agent.

As already described above, the preservatives of groups (a) and (b) and also the further preferred combinations from groups (a), (b) and (d) can also be very suitably used to preserve coloring agents which include oxidation dye precursors.

In a further particularly preferred embodiment, a product according to the invention for changing the color of keratin fibers is characterized in that the coloring preparation (F) includes at least (c) one oxidation dye precursor.

As oxidation dye precursors, use is usually made of developer components or developers in combination with coupler components or couplers. Developers and couplers react with one another under the effect of hydrogen peroxide and form the actual dyes through oxidative coupling.

Suitable developer components are selected from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxa-decane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically acceptable salts of these compounds. Among these, particularly preferred additional developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine and/or 4,5-diamino-1-(2-hydroxyethyl)pyrazole and the physiologically acceptable salts thereof.

Suitable coupler components can be selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2, 6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}-amino)ethanol, 2-[3-morpholin-4-ylphenyl)amino]ethanol, 3-amino-4-(2-methoxy-ethoxy)-5-methylphenyl amine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxy-pyridine, 3-amino-2-methylamino-6-methoxypyridine, 2, 6-dihydroxy-3,4-dimethylpyridine, 3,5-diamino-2, 6-dimethoxypyridine, 1-phenyl-3-methylpyrazol-5-one, 1-naphthol, 1, 5-dihydroxynaphthalene, 2,7-dihydroxynaphthalene, 1,7-dihydroxynaphthalene, 1, 8-dihydroxynaphthalene, 4-hydroxyindole, 6-hydroxyindole, 7-hydroxyindole, 4-hydroxyindoline, 6-hydroxyindoline and/or 7-hydroxyindoline and the physiologically acceptable salts thereof.

The developer(s) may be included in the coloring preparation (F) according to the invention in a total amount of 0.0001 to 5.0% by weight, preferably 0.01 to 2.5% by weight, more preferably 0.05 to 1.0% by weight and very particularly preferably 0.1 to 0.9% by weight, based on the total weight of the agent.

The coupler(s) may be included in the coloring preparation (F) according to the invention in a total amount of 0.0001 to 5.0% by weight, preferably 0.01 to 2.5% by weight, more preferably 0.05 to 1.0% by weight and very particularly preferably 0.1 to 0.9% by weight, based on the total weight of the agent.

The coloring preparations according to the invention may also include further active substances, auxiliaries and additives, such as for example nonionic, anionic, cationic, zwitterionic or amphoteric surfactants and/or emulsifiers, fatty substances such as fatty alcohols, fatty acid esters or hydrocarbons, nonionic, cationic or anionic polymers, further thickening agents, structurants such as glucose, maleic acid and lactic acid, hair-conditioning compounds, perfume oils, dimethyl isosorbide and cyclodextrins, solvents and solubilizing agents, fiber-structure-improving active substances, particularly mono-, di- and oligosaccharides such as for example glucose, galactose, fructose, fruit sugar and lactose, quaternized amines such as methyl-1-alkylamidoethyl-2-alkylimidazolinium methosulfate, defoaming agents such as silicones, colorants for coloring the agent, amino acids and oligopeptides, in particular arginine and/or serine, animal- and/or plant-based protein hydrolysates, such as for example elastin, collagen, keratin, silk and lactoprotein protein hydrolysates, or almond, rice, pea, potato and wheat protein hydrolysates, as well as in the form of their fatty acid condensation products or optionally anionically or cationically modified derivatives, plant oils, for example macadamia nut oil, kukui nut oil, palm oil, amaranth seed oil, peach kernel oil, avocado oil, olive oil, coconut oil, rape oil, sesame oil, jojoba oil, soybean oil, peanut oil, evening primrose oil and tea tree oil, light stabilizers, in particular derivatized benzophenones, cinnamic acid derivatives and triazines, substances for adjusting the pH, such as for example conventional acids, in particular edible acids and bases, active substances such as panthenol, pantothenic acid, pantolactone, allantoin, pyrrolidinonecarboxylic acids, and salts thereof, as well as bisabolol, polyphenols, plant extracts, cholesterol, consistency adjusters such as sugar esters, polyol esters or polyol alkyl ethers, waxes such as spermaceti, beeswax, montan wax and paraffins, fatty acid alkanolamides, swelling and penetration agents such as glycerol, propylene glycol monoethyl ether, carbonates, hydrogen carbonates, guanidines, ureas and primary, secondary and tertiary phosphates, opacifiers such as latex, styrene/PVP and styrene/acrylamide copolymers, pearlescent agents such as ethylene glycol mono- and distearate and PEG-3 distearate, pigments, stabilizers for hydrogen peroxide and other oxidizing agents, propellants such as propane/butane mixtures, $N_2O$, dimethyl ether, $CO_2$ and air, antioxidants.

A person skilled in the art will choose these further substances according to the desired properties of the agents.

With regard to further optional components and the employed amounts of said components, reference is expressly made to the relevant handbooks known to the person skilled in the art, for example Kh. Schrader, Grundlagen and Rezepturen der Kosmetika, 2nd edition, Hüthig Buch Verlag, Heidelberg, 1989.

According to the invention, the cosmetic products described above are used in particular for coloring roots, wherein the coloring of the roots is an additional coloring which takes place between two regular coloring procedures carried out on the full head of hair. Damaging or hair-stressing ingredients are therefore as far as possible omitted from the coloring preparation (F) in order to avoid cumulative hair damage.

Preferably, therefore, the content of alkalizing agents in the coloring preparation (F) is also reduced as far as possible. For this reason, it is also particularly preferred to adjust the coloring preparation (F) to a neutral or at most slightly alkaline pH. Preferably, the pH of the water-containing coloring preparation (F) is therefore at a pH from 4.5 to 9.5, preferably from 5.0 to 9.0, more preferably from 5.5 to 8.7 and very particularly preferably from 6.0 to 8.5.

In a further particularly preferred embodiment, a product according to the invention for changing the color of keratin fibers is characterized in that the coloring preparation (F) is aqueous and has a pH of 4.5 to 9.5, preferably 5.0 to 9.0, more preferably 5.5 to 8.7 and very particularly preferably 6.0 to 8.5.

The pH is usually adjusted by pH adjusters. The person skilled in the art is familiar with acidifying and alkalizing agents common in the cosmetics sector for adjusting the pH. The alkalizing agents which can be used to adjust the pH are typically selected from inorganic salts, organic alkalizing agents, in particular amines, basic amino acids and alkanolamines, and ammonia. Acidifying agents which are preferred according to the invention are edible acids, such as for example citric acid, acetic acid, malic acid or tartaric acid, as well as dilute mineral acids. The pH values in the context of the present invention are pH values which have been measured at a temperature of 22° C. using a glass electrode.

Organic alkalizing agents which can be used according to the invention are preferably selected from alkanolamines of primary, secondary or tertiary amines having a $C_2$-$C_6$ alkyl main body which carries at least one hydroxyl group. Particularly preferred alkanolamines are selected from the group consisting of 2-aminoethan-1-ol (monoethanolamine), 2-amino-2-methylpropan-1-ol, 2-amino-2-methylpropane-1,3-diol and triethanolamine.

In the context of the investigations carried out for the present invention, however, it has been found that agents which are preferred according to the invention are also characterized in that they additionally include an inorganic alkalizing agent. The inorganic alkalizing agent according to the invention is preferably selected from the group formed of sodium hydroxide, potassium hydroxide, calcium hydroxide, barium hydroxide, sodium phosphate, potassium phosphate, sodium silicate, potassium silicate, sodium carbonate and potassium carbonate. Very particular preference is given to sodium hydroxide and/or potassium hydroxide.

The basic amino acids which can be used as the alkalizing agent according to the invention are preferably selected from the group formed of L-arginine, D-arginine, D/L-arginine, L-lysine, D-lysine, D/L-lysine. In the context of the invention, the alkalizing agent used is particularly preferably L-arginine, D-arginine or D/L-arginine.

Finally, a further preferred alkalizing agent is ammonia.

The alkalizing agents are preferably included in an amount of 0.05 to 10% by weight, in particular 0.5 to 5% by weight, in each case based on the total weight of the coloring preparation (F).

As already described above, the cosmetic products according to the invention are particularly suitable for coloring the roots of the hair.

A second subject matter of the present invention is therefore a method for changing the color of the hair at the roots of the hair, comprising the following steps in the specified order (I) withdrawing a portion of a coloring preparation (F) from the reclosable container (C) of the cosmetic product as described in detail in the description of the first subject matter of the invention, (II) optionally mixing the coloring preparation (F) with a preparation which includes an oxidizing agent, so as to obtain the ready-to-use oxidative coloring preparation, (III) applying the (oxidative) coloring preparation (F) to the hair in the region of the roots of the hair, (IV) leaving the coloring preparation (F) to act for a duration of from 30 seconds to 45 minutes, preferably for 1 to 15 minutes, (V) washing out the (oxidative) coloring preparation (F) from the region of the roots.

In the context of the method according to the invention, first a portion of the coloring preparation (F) is withdrawn from the reclosable container. By way of example, by pressing a tube-shaped container (C), the user can transfer the coloring preparation (F) directly onto an applicator or else into a bowl. It is also possible to place a portion of the coloring preparation (F) onto a (gloved) hand.

If the coloring preparation (F) includes at least one oxidation dye precursor (c), it is mixed (according to the optional step (II) of the method according to the invention) with an oxidizing agent preparation, which preferably includes hydrogen peroxide as the oxidizing agent, before being applied to the hair.

Usually, hydrogen peroxide is used as the oxidizing agent. In one preferred embodiment, the hydrogen peroxide is used as an aqueous solution. Oxidizing agent preparations which are preferred according to the invention are characterized in that they include 0.5 to 6.5% by weight, preferably 1.3 to 5.5% by weight, more preferably 2.2 to 5.0% by weight and particularly preferably 3.5 to 4.7% by weight hydrogen peroxide (calculated as 100% strength $H_2O_2$).

If the coloring preparation (F) has been mixed beforehand with an oxidizing agent preparation, it is referred to as an oxidative coloring preparation in the context of the present invention. However, there is preferably no need for an oxidizing agent in the context of the method according to the invention.

Very particular preference is therefore given to a method for changing the color of the hair at the roots of the hair, comprising the following steps in the specified order (Ia) withdrawing a portion of a coloring preparation (F) from the reclosable container (C) of the cosmetic product as described in detail in the description of the first subject matter of the invention, (IIa) applying the coloring preparation (F) to the hair in the region of the roots of the hair, (IIa) leaving the coloring preparation (F) to act for a duration of from 30 seconds to 45 minutes, preferably for 1 to 15 minutes, (IVa) washing out the (oxidative) coloring preparation (F) from the region of the roots.

In the next step (III) of the method according to the invention, the (oxidative) coloring agent is applied to the region at the non-colored roots of the hair. This application preferably takes place using an applicator which is tailored in terms of its dimensions to the width of the roots of the hair (for example a narrow comb having a width of 0.5 to 3 cm or a small narrow sponge having a width of 0.5 to 3 cm). Users who find it difficult to use an applicator can also apply the (oxidative) coloring preparation to the root region directly using a gloved hand.

A characterizing feature of the method according to the invention is the application of the ready-to-use coloring preparation exclusively to the region of the roots of the hair, that is to say that the method according to the invention is not intended for coloring a full head of hair.

The (oxidative) coloring preparation is then applied for a duration of from 30 seconds to 45 minutes. In order to make the coloring of the roots, which is carried out as an intermediate coloring procedure, as convenient as possible, the leave-in time is particularly preferably 1 to 15 minutes.

Thereafter, the (oxidative) coloring agent is then washed out again from the region of the roots of the hair. It may be washed out using tap water or else using a shampoo.

One very particularly preferred method is characterized in that the root coloring procedure is carried out at least two times in succession. In this way, it is possible for the user to draw out for as long as possible the time at which the next coloring of the full head of hair is necessary. In this way, the user's hair also suffers less cumulative hair damage since in each case only the root region of the hair is colored during the root coloring procedure.

With very particular preference, therefore, a method for repeatedly changing the color of the hair at the roots of the hair is characterized in that the above-described steps (I) to (V) (or (Ia) to (IVa)) are carried out at least twice within a period of 4 weeks, wherein the coloring preparation (F) is repeatedly withdrawn in portions from the same reclosable container (C).

With regard to further preferred embodiments of the method according to the invention, what has been stated in relation to the cosmetic products according to the invention applies mutatis mutandis.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic product for changing the color of keratin fibers, in particular human hair, includes
   a coloring preparation (F) which is packaged in a reclosable container (C) for treating hair multiple times, wherein the coloring preparation (F) includes, in a cosmetic carrier,
   (a) at least one first preservative selected from the group consisting of sodium sulfite, potassium sulfite, potassium hydrogen sulfite, sodium hydrogen sulfite, zinc pyrithione, benzoic acid, salicylic acid, sorbic acid, formic acid, propionic acid and the physiologically acceptable salts of the aforementioned acids, and
   (b) at least one second preservative selected from the group consisting of 2-phenoxy-ethanol, and 1-phenoxypropan-2-ol, and
   (c) at least one dye, the dye selected from a group consisting of anionic, cationic and nonionic substantive dyes,
   wherein a weight ratio (a)/(b) of all the preservatives (a) included in the coloring preparation (F) to all the preservatives (b) included in the coloring preparation (F), is 10.0 to 0.1,
   wherein the coloring preparation (F) further includes at least one preservative selected from the group consisting of
   2-hydroxydiphenyl, dehydroacetic acid, dibromohexamidine, 10-undecylenic acid, hexetidinum, triclocarban, triclosanum, 1-(4-chlorophenoxy)-1-(imidazol-1-yl)-3,3-dimethyl-2-butanone, 1,3-bis-(hydroxymethyl)-5,5-dimethyl-2,4-imidazolidinedione, 1-hydroxy-4-methyl-6-(2,4,4-trimethylpentyl)-2-pyridone, 3-methyl-4-(1-methylethyl)phenol, 5-chloro-2-methyl-3(2H)-isothiazolone, 2-benzyl-4-chlorophenol, 2-chloroacetamide, chlorhexidine, 4,4-dimethyl-1,3-oxazolidine, 1-phenoxypropan-2-ol, hexamidinum, 5-ethyl-1-aza-3,7-dioxabicyclo-[3.3.0]-octane, chlorphenesin, sodium hydroxy-methyl aminoacetate, benzyl hemiformal, 3-iodo-2-propynyl butylcarbamate, methylisothiazolinone and Ethyl Lauroyl Arginate, and wherein the cosmetic product comprises no further container containing hydrogen peroxide.

2. The product according to claim 1, wherein the reclosable container (C) is a tube or bottle which is closed by a screw cap and which enables withdrawal of the coloring preparation (F) in portions.

3. The product according to claim 1, further including an applicator for applying the coloring preparation (F) to the roots of the hair.

4. The cosmetic product according to claim 1, wherein the coloring preparation (F) includes the preservatives (a) and (b) in a total amount that has a preserving effect.

5. The product according to claim 1, wherein the weight ratio (a)/(b) is 2.5 to 0.4.

6. The product according to claim 1, wherein the coloring preparation (F) includes—based on the total weight of the coloring preparation (F)—the one or more preservatives (a) in a total amount of 0.05 to 4.5% by weight.

7. The product according to claim 6, wherein the coloring preparation (F) includes—based on the total weight of the coloring preparation (F)—the one or more preservatives (a) in a total amount of 0.2 to 0.7% by weight.

8. The product according to claim 1, wherein the coloring preparation (F) includes—based on the total weight of the coloring preparation (F)—the one or more preservatives (b) in a total amount of 0.1 to 7.0% by weight.

9. The product according to claim 8, wherein the coloring preparation (F) includes—based on the total weight of the coloring preparation (F)—the one or more preservatives (b) in a total amount of 0.7 to 2.5% by weight.

10. The product according to claim 1, wherein the coloring preparation (F) is aqueous and has a pH of 4.5 to 9.5.

11. A method for changing the color of the hair at the roots of the hair, comprising the following steps in the specified order:
(I) withdrawing a portion of a coloring preparation (F) from the reclosable container (C) of the cosmetic product as described in claim 1,
(II) optionally mixing the coloring preparation (F) so as to obtain the ready-to-use coloring preparation,
(III) applying the coloring preparation (F) to the hair in the region of roots of the hair,
(IV) leaving the coloring preparation (F) to act for a duration of from 30 seconds to 45 minutes, and
(V) washing out the coloring preparation (F) from the region of the roots.

12. The method for repeatedly changing the color of the hair at the roots of the hair according to claim 11, wherein steps (I) to (V) are carried out at least twice within a period of 4 weeks, and wherein the coloring preparation (F) is repeatedly withdrawn in portions from the same reclosable container (C).

13. A cosmetic product for changing the color of keratin fibers, in particular human hair, includes a coloring preparation (F) which is packaged in a reclosable container (C) for treating hair multiple times, wherein the coloring preparation (F) includes, in a cosmetic carrier,
(a) at least one first preservative selected from the group consisting of potassium sulfite, potassium hydrogen sulfite, zinc pyrithione, benzoic acid, salicylic acid, sorbic acid, formic acid, propionic acid and the physiologically acceptable salts of the aforementioned acids, and
(b) at least one second preservative selected from the group consisting of 2-phenoxy-ethanol, benzyl alcohol, 1-phenoxypropan-2-ol, isopropanol and ethanol, and
(c) at least one substantive dye, the dye selected from a group consisting of anionic, cationic and nonionic substantive dyes,
wherein a weight ratio (a)/(b) of all the preservatives (a) included in the coloring preparation (F) to all the preservatives (b) included in the coloring preparation (F), is 10.0 to 0.1, and
wherein the coloring preparation (F) further includes at least one preservative selected from the group consisting of
2-hydroxydiphenyl, dehydroacetic acid, dibromohexamidine, 10-undecylenic acid, hexetidinum, triclocarban, triclosanum, 1-(4-chlorophenoxy)-1-(imidazol-1-yl)-3,3-dimethyl-2-butanone, 1,3-bis-(hydroxymethyl)-5,5-dimethyl-2,4-imidazolidinedione, 1-hydroxy-4-methyl-6-(2,4,4-trimethylpentyl)-2-pyridone, 3-methyl-4-(1-methylethyl)phenol, 5-chloro-2-methyl-3(2H)-isothiazolone, 2-benzyl-4-chlorophenol, 2-chloroacetamide, chlorhexidine, 4,4-dimethyl-1,3-oxazolidine, 1-phenoxypropan-2-ol, hexamidinum, 5-ethyl-1-aza-3,7-dioxabicyclo-[3.3.0]-octane, chlorphenesin, sodium hydroxy-methyl aminoacetate, benzyl hemiformal, 3-iodo-2-propynyl butylcarbamate, methylisothiazolinone and Ethyl Lauroyl Arginate, and
wherein the cosmetic product comprises no further container containing hydrogen peroxide.

14. The product according to claim 13, wherein the coloring preparation (F) includes at least two first preservatives (a) selected from the group consisting of potassium sulfite, potassium hydrogen sulfite, zinc pyrithione, benzoic acid, salicylic acid, sorbic acid, formic acid, propionic acid and the physiologically acceptable salts of the aforementioned acids.

15. The product according to claim 1, wherein the coloring preparation (F) includes the at least one first preservative (a) selected from the group consisting of potassium sulfite, potassium hydrogen sulfite, zinc pyrithione, benzoic acid, salicylic acid, sorbic acid, formic acid, propionic acid and the physiologically acceptable salts of the aforementioned acids.

16. The product according to claim 15, wherein the coloring preparation (F) includes at least two preservatives (a) selected from the group consisting of potassium sulfite, potassium hydrogen sulfite, zinc pyrithione, benzoic acid, salicylic acid, sorbic acid, formic acid, propionic acid and the physiologically acceptable salts of the aforementioned acids.

* * * * *